United States Patent
Zhang et al.

(12) 
(10) Patent No.: US 7,323,178 B1
(45) Date of Patent: Jan. 29, 2008

(54) METHOD OF IDENTIFICATION OF EQUINE HERPES VIRUS TYPE 1 CAUSING NEUROLOGICAL DISEASE, METHOD OF PRODUCING A VACCINE AGAINST NEUROLOGICAL DISEASE CAUSED BY EQUINE HERPES VIRUS TYPE 1, AND VACCINE AGAINST NEUROLOGICAL DISEASE CAUSED BY EQUINE HERPES VIRUS TYPE 1

(75) Inventors: Yan Zhang, New Albany, OH (US); Sree Kumari Rajeev, Pickerington, OH (US); Beverly Byrum, Grove City, OH (US)

(73) Assignee: The Ohio Department of Agriculture, Reynoldsburg, OH (US)

( * ) Notice: Subject to any disclaimer, the term of this patent is extended or adjusted under 35 U.S.C. 154(b) by 300 days.

(21) Appl. No.: 11/027,151

(22) Filed: Dec. 29, 2004

Related U.S. Application Data

(60) Provisional application No. 60/536,880, filed on Jan. 16, 2004.

(51) Int. Cl.
*A61K 39/245* (2006.01)
(52) U.S. Cl. .............................. 424/229.1; 424/204.1; 435/69.1
(58) Field of Classification Search ............. 424/229.1, 424/204.1, 130.1; 435/6, 69.1, 7.1, 345
See application file for complete search history.

(56) References Cited

U.S. PATENT DOCUMENTS

| | | | |
|---|---|---|---|
| 6,083,511 | A | 7/2000 | Onions et al. ............ 424/229.1 |
| 6,193,983 | B1 | 2/2001 | Crabb et al. ............. 424/229.1 |
| 6,225,111 | B1 | 5/2001 | Cochran et al. ......... 435/320.1 |
| 6,248,333 | B1 | 6/2001 | Paoletti .................... 424/229.1 |
| 6,395,283 | B1 | 5/2002 | Paoletti .................... 424/229.1 |
| 6,544,526 | B1 | 4/2003 | Crabb et al. ............. 424/199.1 |

OTHER PUBLICATIONS

Brown Kimberly. The Horse.com, May 2005, pp. 1-3.*

* cited by examiner

*Primary Examiner*—Ali R. Salimi
(74) *Attorney, Agent, or Firm*—Roger A. Gilcrest

(57) ABSTRACT

Equine herpesvirus type 1 (EHV-1) causes abortion and respiratory infection in horses. Only certain strains of EHV-1 cause encephalitis. Vaccination of horses with live attenuated or inactivated vaccines against EHV-1 is commonly practiced using commercial vaccine products. None of those vaccines have been tested for protection of horses against neurologic manifestation caused by EHV-1. Clinical evidence indicates that horses vaccinated with the commercial vaccines were protected against the respiratory diseases caused by EHV-1. However, the vaccinated horses were not protected against neurological disease. In this invention, we describe the development of a new inactivated EHV-1 vaccine. The new vaccine will protect vaccinated horses against neurological disease as well as respiratory disease and abortion caused by EHV-1. The vaccine will use a newly isolated Findlay strain of EHV-1 as the master seed virus. This virus was extremely virulent and caused high morbidity (>80%) in a well-vaccinated horse population. This virus was highly neurotropic as over 30% of the sick animals developed neurologic disease. The vaccine is formatted with the Findlay strain of EHV-1 and alum as adjuvant.

20 Claims, 1 Drawing Sheet

Figure 1. Partial sequence of the Findlay strain of EHV-1

CGACGAACTCGTCAGGGACGAGTTCCGCGGGTCCTACAGATTTACTATTCGATCCATCTCGTCTACG

TTTATCAGTAACACTACTCAATTTAAGTTGGAAAGTGCCCCCCTTACTGAATGTGTATCCAAAGAAGC

AAAGGAAGCCATAGACTCGATATACAAAAAGCAGTACGAGTCTACGCACGTCTTTAGCGGTGATGTG

GAATATTACCTGGCACGCGGGGGGTTCTTAATTGCATTCAGACCTATGCTCTCCAACGAACTCGCCA

GGCTGTACCTGAACGAGCTTGTGAGATCTAACCGCACCTACGACCTAAAAAATCTATTGAACCCCAA

TGCAAACAATAACAATAACACCACGCGAAGACGCAGGTCTCTCCTGTCAGTACCAGAACCTCAGCCA

ACCCAAGATGGTGTGCATAGAGAACAAATTCTACATCGCTTGCACAAACGAGCAGTGGAGGCAACG

GCAGGTACCGATTCTTCCAGCGTCACCGCCAAACAGCTGGAGCTCATCAAAACCACGTCGTCTATCG

AGTTTGCATGCTACAG

```
                         SEQUENCE LISTING

<160> NUMBER OF SEQ ID NOS: 1

<210> SEQ ID NO 1
<211> LENGTH: 552
<212> TYPE: DNA
<213> ORGANISM: Equine herpesvirus 1
<220> FEATURE:
<221> NAME/KEY: misc_structure
<222> LOCATION: (1)..(552)
<223> OTHER INFORMATION: Sequence used for identification of EHV-1
      Equine Herpes virus.

<400> SEQUENCE: 1
cgacgaactc gtcagggacg agttccgcgg gtcctacaga tttactattc gatccatctc     60
gtctacgttt atcagtaaca ctactcaatt taagttggaa agtgcccccc ttactgaatg    120
tgtatccaaa gaagcaaagg aagccataga ctcgatatac aaaaagcagt acgagtctac    180
gcacgtcttt agcggtgatg tggaatatta cctggcacgc gggggttct taattgcatt    240 cagacctatg ctctccaacg aactcgccag gctgtacctg aacgagcttg tgagatctaa    300
ccgcacctac gacctaaaaa atctattgaa ccccaatgca aacaataaca ataacaccac    360
gcgaagacgc aggtctctcc tgtcagtacc agaacctcag ccaacccaag atggtgtgca    420
tagagaacaa attctacatc gcttgcacaa acgagcagtg gaggcaacgg caggtaccga    480
ttcttccagc gtcaccgcca aacagctgga gctcatcaaa accacgtcgt ctatcgagtt    540
tgcatgctac ag                                                        552
```

METHOD OF IDENTIFICATION OF EQUINE HERPES VIRUS TYPE 1 CAUSING NEUROLOGICAL DISEASE, METHOD OF PRODUCING A VACCINE AGAINST NEUROLOGICAL DISEASE CAUSED BY EQUINE HERPES VIRUS TYPE 1, AND VACCINE AGAINST NEUROLOGICAL DISEASE CAUSED BY EQUINE HERPES VIRUS TYPE 1

RELATED APPLICATION DATA

The present invention claims priority from U.S. Provisional Patent Application No. 60/536,880, filed Jan. 16, 2004, which is incorporated hereby by reference in its entirety.

FIELD OF THE INVENTION

This invention relates to a virus detection method and improved vaccine for the protection of horses against EHV-1 infection, especially neurologic diseases caused by the viruses.

BACKGROUND OF THE INVENTION

Equine herpesvirus type 1 (EHV-1) causes abortion and respiratory infection that are extremely dangerous health risk for domestic horses of all ages and categories, as well as for other members of Equidae family. Only certain strains of EHV-1 cause encephalitis.

Vaccination of horses with live attenuated or inactivated vaccines against EHV-1 is commonly practiced using commercial vaccine products. In the USA, there are currently eight commercial vaccines that are manufactured by four veterinary biological manufacturers. The vaccines are produced to contain a single strain of EHV-1, multiple strain of EHV-1, combination of both EHV-1 and equine herpesvirus type 4 (EHV-4) available, or combination of EHV-1, EHV-4, and equine influenza virus subtypes type 1 and 2. Those vaccines are, in general, effective against respiratory infection although the duration of immunity is short and frequent immunization is required. Several attempts to identify and vaccinate against equine herpes are described in U.S. Pat. Nos. 6,544,526; 6,395,283; 6,248,333; 6,225,111; 6,193,983; and 6,083,511; which are hereby incorporated herein by reference.

However, none of those vaccines have been tested for protection of horses against neurologic disease caused by EHV-1. Clinical evidence indicates that immunization of horses with those marketed vaccines do not provide protection against neurologic disease caused by the neurotropic strains of EHV-1. During the EHV-1 outbreak in Findlay, Ohio, which occurred in January 2003, eighty-eight percent (119/135) of previously well-vaccinated horses were clinically affected with mild upper respiratory disease and/or fever, indicating the horses were protected against the clinical respiratory disease caused by EHV-1. However, over forty horses developed neurological signs. Among them, 12 horses died or were euthanized due to the severe neurological disease.

A vaccine composed of a neurotropic strain of EHV-1 or its component alone or in combination with other strains of EHV-1 may be used to provide protection against EHV-1 infection and neurologic disease caused by the neurotropic strain of EHV-1. Thus, a vaccine that contains a neurotropic stain of EHV-1 or its component and will overcome the drawback of the commercial vaccine and protect equine species against neurologic disease in addition to respiratory infection and abortion caused by EHV-1. It would be likely that the most appropriate vaccine uses a strain of virus derived from a neurotropic strain of EHV-1 for the protection of horses against neurologic disease as well as other clinical diseases caused by the virus. Here, we describe our invention of a vaccine against infection and neurologic disease caused by EHV-1.

SUMMARY OF THE INVENTION

The object of this invention is to provide methods for diagnosing and vaccinating against clinical diseases especially the neurologic disease caused by EHV-1.

The invention includes methods of determining the presence of the Findlay strain of EHV-1, including methods to determine its presence as against other EHV-1 strains. Also included are compositions of matter useful in that determination, and vaccines and methods of vaccination against infection caused by neurotropic strain of EHV-1.

The Findlay strain was deposited pursuant to, and in satisfaction of, the requirements of the Budapest Treaty on the International Recognition of the Deposit of Microorganisms for the Purposes of Patent Procedure with the American Type Culture Collection (ATCC), 10801 University Blvd., Manassas, Va. 20110-2209 under ATCC Accession No. PTA-5789. The Findlay strain was deposited with the ATCC on Jan. 15, 2004, and is identified by Accession No. PTA-5789 ATCC PTA-5789 and is hereby incorporated herein by reference. As proof of the deposit, we have attached a copy of the ATCC Budapest Treaty Deposit Form (BP1) and the American Type Culture Collection along with the United States Veterinary Permit for Importation and Transportation of Controlled Materials and Organisms and Vectors and a copy of the FedEx Express USA Airbill (Tracking No. 8447 0633 0834).

The present invention includes a vaccine based on the Findlay strain of EHV-1, preferably in an inactivated form and administered using alum as adjuvant intramuscularly or subcutaneously. The vaccine protects against infection and resulting neurologic disease caused by EHV-1.

The vaccine of the present invention will use a newly isolated neurotropic strain of EHV-1 (designated as Findlay strain) as the master seed virus and formulated with alum as adjuvant. This vaccine can also be used in combination with those for other viruses including EHV-1, EHV-4, equine influenza virus type 1 and 2 and/or equine viral arteritis virus (EVA) to provide protection against respiratory diseases and abortion caused by those agents.

The master seed virus (MSV) for the vaccine is Findlay strain of EHV-1. The virus was originally isolated by the Ohio Animal Disease diagnostic Laboratory during an outbreak in January 2003. The virus was isolated using standard techniques, and may be positively identified to be an EHV-1 by fluorescent conjugated anti-EHV-1 polyclonal or monoclonal antibody (FA), by EHV-1 specific PCR amplification, and by DNA sequence analysis. The vaccine may be prepared by any appropriate technique such as by growing the virus in a RK-13 cell line for 48 hours, inactivated, and formulated with alum as adjuvant. Inactivation of the viruses may be achieved by the use of 0.2% beta propiolactone for 24 hours at 4° C.

The vaccine may be administered using any appropriate technique for horses, such as by intramuscular or subcutaneously injection. Preferably, initially two doses are given one month apart, followed by boosters every six months.

Pregnant mares may be vaccinated every two months during the first two trimesters of gestation.

The Findlay strain may also be used in accordance with other methods, techniques and compositions in accordance with known uses of other EHV-1 strains.

Accordingly, in general terms, the invention includes a vaccine based on the highly virulent EHV-1, ATCC Accession No. PTA-5789, against neurologic disease as well as respiratory disease and abortion, in an inactivated or attenuated form. The invention also includes a vaccine for a strain of EHV-1, ATCC Accession No. PTA-5789 that produces both neurologic disease and respiratory disease in equine animals, which may be the strain of EHV-1, ATCC Accession No. PTA-5789 is in an inactivated or attenuated form.

It is preferred that the vaccine is additionally comprises an adjuvant, preferably alum.

The invention also includes a combined vaccine for a strain of EHV-1, ATCC Accession No. PTA-5789, and for any other viruses selected from the group consisting of equine viruses, in an inactivated or attenuated live virus form, such as a combined vaccine wherein the at least one other virus is selected from the group consisting of equine influenza viruses and equine viral arteritis virus.

The combined vaccine preferably also includes an adjuvant, preferably alum.

Also included in the present invention is a method of vaccination against neurologic disease caused by a strain of equine herpes viruses comprising administering an effective amount of a vaccine as described herein. The vaccine may be administered by injecting intramuscularly or subcutaneously.

The invention also includes any vaccine or vaccine derivative derived from the strain of EHV-1, ATCC Accession No. PTA-5789, as well as an isolated strain of EHV-1, ATCC Accession No. PTA-5789. The invention also includes an epitope that elicits a type-specific response to EHV-1, ATCC Accession No. PTA-5789.

The invention further includes any immunogenic composition comprising an immunogenic amount of an epitope of the strain of EHV-1, ATCC Accession No. PTA-5789 in a physiologically acceptable vehicle, such as the attenuated virus in a physiologically acceptable vehicle.

The invention also includes an immunological test kit for screening for infection of a horse by the strain of EHV-1, ATCC Accession No. PTA-5789 comprising as a capture antigen or EHV-1 epitope(s) that elicits a type-specific response to EHV-1, ATCC Accession No. PTA-5789.

Also part of the present invention is a method of vaccinating against a neurologic disease caused by the strain of EHV-1, ATCC Accession No. PTA-5789, comprising the steps: (a) obtaining access to an equine animal subject to neurologic disease caused by infection by the strain of EHV-1, ATCC Accession No. PTA-5789; and (b) administering an immunogenic composition comprising an immunogenic amount of the epitope(s) of the strain of EHV-1, ATCC Accession No. PTA-5789 in a physiologically acceptable vehicle, such as an attenuated virus of the strain of EHV-1, ATCC Accession No. PTA-5789.

The invention also comprises a method of diagnosing a neurologic disease caused by the strain of EHV-1, ATCC Accession No. PTA-5789, comprising the steps: (a) obtaining a sample, such as biological fluid, from an equine animal subject to potential infection by the strain of EHV-1, ATCC Accession No. PTA-5789, and (b) determining the presence or absence of the strain of EHV-1, ATCC Accession No. PTA-5789, in the equine animal.

The presence or absence of the strain of EHV-1, ATCC Accession No. PTA-5789, is done by any method such as those selected from the group consisting of fluorescent conjugated anti-EHV-1 monoclonal antibody or by EHV-1 specific PCR amplification.

DESCRIPTION OF PREFERRED EMBODIMENTS

In accordance with the foregoing summary, the following describes a preferred embodiment of the present inventions, which are considered to be the best mode.

1. Seed Management a) Master Seed Virus (MSV) Characteristic and Culture

The Findlay strain of virus was originally isolated in the laboratory and selected as the primary MSV for the vaccine. The isolate was confirmed by FA, EHV-1 specific PCR, and DNA sequence analysis based on equine herpesvirus type 1 glycoprotein 14 (gp14) gene. The partial sequence of gp14 of the Findlay strain virus is 99% identical to the same gene (or gB gene) of other strains of EHV-1 (RacH and Rac111 strains), 95% to Gazelle herpesvirus-1, and only 83% homologous to EHV-4. The partial sequence of the Findlay strain of EHV-1 is shown in FIG. 1.

The Findlay strain can be used alone as a vaccine, or combined with other stains of strain of EHV-1 (ATCC # VR 2229) and/or administered with EHV-4 (ATCC # 2230).

The seed virus(es) may be cultured using, for instance, rabbit kidney cell line (RK-13) cells as master cell stock or MSC (ATCC # CCL-37) or other appropriate cell line. The medium for viral propagation is ATCC medium: minimum essential medium (Eagle) containing 2 mM L-gluamine and Earle's BSS adjusted to contain 1.5 g/L sodium bicarbonate, 0.1 mM non-essential amino acids, and 1.0 mM sodium 90% pyruvate, and 10% fetal bovine serum.

b) Purity

The purity of MSV may be determined to be free from bacteria, fungi, and mycoplasmas by standard methods. Specific tests may be performed to confirm the absence of equine infectious anaemia virus, equine rhinoviruses, equine influenza virus, equine viral arteritis virus, equine herpes virus type-2, -3, -4, and -5, Eastern, Western, and Venezuela equine encephalomyelitis viruses, porcine parvovirus, and bovine viral diarrhea virus by RT-PCR/PCR specific for each virus.

2. Method of Manufacture

The medium may be seeded with 100 $TCID_{50}$ of the virus (maximum passage of MSV is five) in 75 ml total volume and cultured at 37° C., 5% $CO_2$ for 2 days. The virus may then be harvested and titer is determined by plaque assay. The virus titer should be equal or exceed 7.5 PFU per ml at $10^{th}$ dilution of 1:10 dilution. The virus may be inactivated by the use of 0.2% beta propiolactone for 24 hours at 4° C.

3. Method of Immunization

The inactivated virus may be adsorbed in 2 mg alum (Rehydragel, low viscosity sterile gel; Reheis, Inc., Berkeley Heights, N.J.) for 1 hour in room temperature and stored at 4° C. The vaccine is administered to horses by intramuscular inoculation for the first 2 injections at one-month interval. The vaccinated horses may be further boosted every six-month. Mares that are pregnant can be vaccinated three times with two-month interval during the first two trimesters of gestation.

While the invention has been described in connection with what is presently considered to be the most practical and preferred embodiments, it is to be understood that the invention is not to be limited to the disclosed embodiment(s), but on the contrary, is intended to cover various modifications and equivalent arrangements included within the spirit and scope of the appended claims, which are incorporated herein by reference.

8. A vaccine according to claim 6 wherein said vaccine is additionally comprises an adjuvant.

9. A vaccine according to claim 8 wherein said adjuvant comprises alum.

10. A method of vaccination against neurologic disease caused by a strain of equine herpes viruses comprising administering an effective amount of a vaccine according to claim 1.

We claim:

1. A vaccine based on the highly virulent EHV-1, ATCC Accession No. PTA-5789, against neurologic disease as well as respiratory disease and abortion, in an inactivated form.

2. A vaccine for a strain of EHV-1, ATCC Accession No. PTA-5789 that produces both neurologic disease and respiratory disease in equine animals.

3. A vaccine according to claim 2 wherein said vaccine contains said strain of EHV-1, ATCC Accession No. PTA-5789 is in an inactivated form.

4. A vaccine according to claim 2 wherein said vaccine is additionally comprises an adjuvant.

5. A vaccine according to claim 4 wherein said adjuvant comprises alum.

6. A combined vaccine for a strain of EHV-1, ATCC Accession No. PTA-5789, and any other viruses selected from the group consisting of equine viruses, in an inactivated or attenuated live virus form.

7. A combined vaccine according to claim 6 wherein said at least one other virus is selected from the group consisting of equine influenza viruses and equine viral arteritis virus.

11. A method according to claim 10 wherein said vaccine is administered by injecting intramuscularly or subcutaneously.

12. A method of vaccination against neurologic disease caused by a strain of equine herpes viruses comprising administering an effective amount of a vaccine according to claim 2.

13. A method according to claim 12 wherein said vaccine is administered by injecting intramuscularly or subcutaneously.

14. A method of vaccination against neurologic disease caused by a strain of equine herpes viruses comprising administering an effective amount of a vaccine according to claim 3.

15. A method according to claim 14 wherein said vaccine is administered by injecting intramuscularly or subcutaneously.

16. A method of vaccinating against a neurologic disease caused by the strain of EHV-1, ATCC Accession No. PTA-5789, comprising the steps:

(a) obtaining access to an equine animal subject to neurologic disease caused by infection by the strain of EHV-1, ATCC Accession No. PTA-5789; and (b) administering an immunogenic composition comprising an immunogenic amount of an epitope of the strain of EHV-1, ATCC Accession No. PTA-5789 in a physiologically acceptable vehicle.

17. A method of vaccinating accordingly to claim 16 wherein said epitope comprises an attenuated virus of the strain of EHV-1, ATCC Accession No. PTA-5789 in a physiologically acceptable vehicle.

18. A method of diagnosing a neurologic disease caused by the strain of EHV-1, ATCC Accession No. PTA-5789, comprising the steps:

(a) obtaining a sample from an equine animal subject to potential infection by the strain of EHV-1, ATCC Accession No. PTA-5789, and (a) determining the presence or absence of the strain of EHV-1, ATCC Accession No. PTA-5789, in said equine animal.

19. A method of diagnosing according to claim 18 wherein said sample is a biological fluid.

20. A method of diagnosing according to claim 18 wherein said determination of the presence or absence of the strain of EHV-1, ATCC Accession No. PTA-5789, is done by a method selected from the group consisting of fluorescent conjugated anti-EHV-1 monoclonal antibody or by EHV-1 specific PCR amplification.

* * * * *